United States Patent
Majeed et al.

(10) Patent No.: US 10,864,243 B1
(45) Date of Patent: Dec. 15, 2020

(54) COMPOSITION FOR PROSTAGLANDIN TRANSPORTER INHIBITION AND RELATED THERAPEUTIC APPLICATIONS

(71) Applicants: Muhammed Majeed, Bangalore (IN); Kalyanam Nagabhushanam, East Windsor, NJ (US); Sarang Bani, Bangalore (IN); Anjali Pandey, Bangalore (IN)

(72) Inventors: Muhammed Majeed, Bangalore (IN); Kalyanam Nagabhushanam, East Windsor, NJ (US); Sarang Bani, Bangalore (IN); Anjali Pandey, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/432,950

(22) Filed: Jun. 6, 2019

(51) Int. Cl.
| | |
|---|---|
| *A61K 36/8962* | (2006.01) |
| *A61K 36/88* | (2006.01) |
| *A61K 36/21* | (2006.01) |
| *A61K 36/71* | (2006.01) |
| *A61K 36/185* | (2006.01) |
| *A61P 9/12* | (2006.01) |
| *A61K 31/122* | (2006.01) |
| *A61K 31/704* | (2006.01) |
| *A61K 31/192* | (2006.01) |
| *A61K 31/197* | (2006.01) |

(52) U.S. Cl.
CPC ............ *A61K 36/88* (2013.01); *A61K 31/122* (2013.01); *A61K 31/192* (2013.01); *A61K 31/197* (2013.01); *A61K 31/704* (2013.01); *A61K 36/185* (2013.01); *A61K 36/21* (2013.01); *A61K 36/71* (2013.01); *A61P 9/12* (2018.01)

(58) Field of Classification Search
None
See application file for complete search history.

(56) References Cited

U.S. PATENT DOCUMENTS 10,479,749 B2 * 11/2019 Majeed ............... C07D 311/60
2019/0160117 A1 * 5/2019 Hillebrand ............ A61K 35/74

OTHER PUBLICATIONS

Mollik A. Plants Used in Popular Medicine for Treatment of Atherosclerosis. Int J Neuropsychopharmacology 15(Suppl 1, p. 244) Abstract P-23-028, Jun. 2012. (Year: 2012).*
Ricciotti et al., Prostaglandins and Inflammation, Arteriosclerosis, Thrombosis, and Vascular Biology, 2011; 31:986-1000.
Harris et al., Prostaglandins as modulators of immunity, Trends in Immunology, 2002; 23(3):144-150.
Wand and DuBois, Prostaglandins and Cancer, Recent advances in basic science, http://dx.doi.org/10.1136/gut.2004.047100.
Anderson et al., Prostaglandins: Effects on blood pressure, renal blood flow, sodium and water excretion, Kidney International, 1976;10(3):205-215.
Klien et al., Prostaglandins: Stimulation of Bone Resorption in Tissue Culture, Endocrinology, 1970; 86(6):1436-1440.
Chi et al., Development of a High-Affinity Inhibitor of the Prostaglandin Transporter, J Pharmacol Exp Ther. 2011;339(2): 633-641.
Ramanlal and Gupta (Physiology, Vasodilation . In: StatPearls [Internet]. Treasure Island (FL): StatPearls Publishing; Available from: https://www.ncbi.nlm.nih.gov/books/NBK557562/).

* cited by examiner

*Primary Examiner* — Ralph J Gitomer (57) ABSTRACT

The present invention discloses a composition comprising *Allium sativum* extract standardized to contain not less that 0.3% w/w S-allylcysteine, *Beta vulgaris* extract standardized to contain not less than 2% w/w nitrates, *Nigella sativa* extract standardized to contain 0.1%-5% w/w thymoquinone, about 0.01%-10% w/w thymohydroquinone, about 20%-95% w/w fatty acids, about 0.001%-3% w/w α-hederin or hederagenin, and *Terminalia arjuna* extract standardized to contain 3% w/w arjunoglucosides for use a prostaglandin transporter inhibitor. The invention also discloses the use of the aforementioned composition in the therapeutic management of hypertension and cardiovascular complications.

3 Claims, 5 Drawing Sheets

COMPOSITION FOR PROSTAGLANDIN TRANSPORTER INHIBITION AND RELATED THERAPEUTIC APPLICATIONS

FIELD OF INVENTION

The invention in general relates to composition comprising plant extracts. More specifically the present invention pertains to compositions for inhibiting prostaglandin transporter (PGT) and related therapeutic applications.

BACKGROUND OF THE INVENTION

Prostaglandins (PGs) are naturally occurring unsaturated fatty acids which are implicated in mediating a variety of pathophysiological processes and homeostatic functions in different organs. They are derived from arachidonic acid by the action of cyclooxygenase isoenzymes. Principally, there are 4 bioactive PGs ubiquitously produced: prostaglandin E2 (PGE2), prostacyclin (PGI2), prostaglandin D2 (PGD2), and prostaglandin F2α (PGF2α), acting as autocrine and paracrine mediators to maintain homeoastatic functions in the body (Ricciotti et al., Prostaglandins and Inflammation, Arteriosclerosis, Thrombosis, and Vascular Biology. 2011; 31:986-1000). PGs play a main role in regulating many disease conditions in the body including inflammation. The biological roles of PGs are well described in the scientific literature some of which are mentioned herein below:
1. Ricciotti et al., Prostaglandins and Inflammation, Arteriosclerosis, Thrombosis, and Vascular Biology, 2011; 31:986-1000.
2. Harris et al., Prostaglandins as modulators of immunity, Trends in Immunology, 2002; 23(3):144-150.
3. Wand and DuBois, Prostaglandins and Cancer, Recent advances in basic science, http://dx.doi.org/10.1136/gut.2004.047100.
4. Anderson et al., Prostaglandins: Effects on blood pressure, renal blood flow, sodium and water excretion, Kidney International, 1976; 10(3):205-215.
5. Klien et al., Prostaglandins: Stimulation of Bone Resorption in Tissue Culture, Endocrinology, 1970; 86(6):1436-1440.

Apart from its role in inflammation, PGs also play a role in ovulation, mucus secretion in GI tract, vasodilatation and angiogenesis. The PGs elicit their function by triggering cascade signals upon binding to its transporter in the cell membrane. Solute carrier organic anion transporter family, member 2A1 is also known as the prostaglandin transporter (PGT) is a member of the 12-membrane-spanning organic anion-transporting polypeptide super family of transporters. The encoded protein is involved in mediating the uptake and clearance of prostaglandins in numerous tissues and organs which include Brain, Colon, Heart, Kidney, Liver, Lung, Ovary, Pancreas, Placenta, Prostate, Skeletal muscle, Small intestine, Spleen and Vascular endothelium. PGT is now increasingly becoming a target for the development of drugs to curtail the harmful effects brought about by the uptake of PGs into the cells and related clinical conditions. Chi et al., in their publication titled Development of a High-Affinity Inhibitor of the Prostaglandin Transporter, J Pharmacol Exp Ther. 2011; 339(2): 633-641, discloses a novel molecule N-(2-(2-(2-azidoethoxy)ethoxy)ethyl)-4-((4-((2-(2-(2-benzamidoethoxy)ethoxy)ethyl)amino)-6-((4-hydroxyphenyl)amino)-1,3,5-triazin-2-yl)amino)benzamide (T26A) for PGT inhibition. Non-steroidal anti-inflammatory drugs (NSAIDs) are also known to inhibit the generation and effect of the PGs. However, these synthetic drugs have increased side effects and there exists a need for a safe and natural alternative to mitigate the effects of PGs by inhibiting PGT. Active molecules derived from plants are now being used extensively for treating many diseases and disorders. However, a plant based composition for inhibiting or blocking PGT is not reported. The present invention solves the above problem by disclosing a natural plant based composition for the inhibition of PGT and to bring about related therapeutic effects.

It is the principle object of the invention to disclose a composition comprising effective doses of *Allium sativum* extract, *Beta vulgaris* extract, *Nigella sativa* extract and *Terminalia arjuna* extract for use a PGT inhibitor.

It is another object of the invention to disclose a method for the therapeutic management of hypertension using a composition comprising *Allium sativum* extract, *Beta vulgaris* extract, *Nigella sativa* extract and *Terminalia arjuna* extract.

It is another object of the invention to disclose a method for conferring cardio protection in mammals using a composition comprising *Allium sativum* extract, *Beta vulgaris* extract, *Nigella sativa* extract and *Terminalia arjuna* extract.

The present invention solves the above objectives and provides further related advantages.

SUMMARY OF THE INVENTION

The present invention provides a natural plant based composition for use as a prostaglandin transporter inhibitor.

More specifically, the invention discloses a composition comprising effective doses of *Allium sativum* extract standardized to contain not less than 0.3% w/w S-allylcysteine, *Beta vulgaris* extract standardized to contain not less than 2% w/w nitrates, *Nigella sativa* extract standardized to contain 0.1%-5% w/w thymoquinone, about 0.01%-10% w/w thymohydroquinone, about 20%-95% w/w fatty acids, about 0.001%-3% w/w α-hederin or hederagenin, and *Terminalia arjuna* extract standardized to contain 3% w/w arjunoglucosides for use a PGT inhibitor The invention also discloses a method for the therapeutic management of hypertension in mammals using a composition comprising *Allium sativum* extract standardized to contain not less than 0.3% w/w S-allylcysteine, *Beta vulgaris* extract standardized to contain not less than 2% w/w nitrates, *Nigella sativa* extract standardized to contain 0.1%-5% w/w thymoquinone, about 0.01%-10% w/w thymohydroquinone, about 20%-95% w/w fatty acids, about 0.001%-3% w/w α-hederin or hederagenin, and *Terminalia arjuna* extract standardized to contain 3% w/w arjunoglucosides.

In another aspect, the invention discloses a method for conferring cardio protection in mammals using a composition comprising *Allium sativum* extract standardized to contain not less than 0.3% w/w S-allylcysteine, *Beta vulgaris* extract standardized to contain not less than 2% w/w nitrates, *Nigella sativa* extract standardized to contain 0.1%-5% w/w thymoquinone, about 0.01%-10% w/w thymohydroquinone, about 20%-95% w/w fatty acids, about 0.001%-3% w/w α-hederin or hederagenin, and *Terminalia arjuna* extract standardized to contain 3% w/w arjunoglucosides.

Other features and advantages of the present invention will become apparent from the following more detailed description, taken in conjunction with the accompanying images, which illustrate, by way of example, the principle of the invention.

DESCRIPTION OF PREFERRED EMBODIMENTS

The invention is described in detail with each preferred embodiment for better understanding and to enable a person moderately skilled in the art to manifest or practice the invention.

In a preferred embodiment, the invention discloses a plant based composition comprising of *Allium sativum* extract, *Beta vulgaris* extract, *Nigella sativa* extract and *Terminalia arjuna* extract. In a related aspect, the *Allium sativum* extract is standardized to contain not less than 0.3% S-allylcysteine. In another related aspect, the *Beta vulgaris* extract is standardized to contain not less than 2% nitrates. In yet another related aspect, the *Nigella sativa* extract is standardized to contain 0.1%-5% w/w thymoquinone, about 0.01%-10% w/w thymohydroquinone, about 20%-95% w/w fatty acids, about 0.001%-3% w/w α-hederin or hederagenin. In another aspect, the *Terminalia arjuna* extract is standardized to contain 3% w/w arjunoglucosides. In another preferred embodiment, the composition is used as prostaglandin transporter inhibitor. In yet another preferred embodiment, the composition is used for the therapeutic management of hypertension. In a further preferred embodiment, the composition is used as a cardio protective agent. In another related aspect, the composition is formulated with pharmaceutically/nutraceutically acceptable bioavailability enhancers, antioxidants, excipients, adjuvants, diluents or carriers and administered in the form of tablets, capsules, syrups, gummies, powders, suspensions, emulsions, chewables, candies or eatables.

In another preferred embodiment, the present invention discloses a method for inhibiting prostaglandin transporter in mammalian cells, said method comprising step of bringing into contact mammalian cells expressing prostaglandin transporter with a composition comprising 30-60% w/w *Allium sativum* extract, 10-30% w/w *Beta vulgaris* extract, 5-15% w/w *Nigella sativa* extract and 10-30% w/w *Terminalia arjuna* extract. In a related aspect, the *Allium sativum* extract is standardized to contain not less than 0.3% S-allylcysteine. In another related aspect, the *Beta vulgaris* extract is standardized to contain not less than 2% nitrates. In yet another related aspect, the *Nigella sativa* extract is standardized to contain 0.1%-5% w/w thymoquinone, about 0.01%-10% w/w thymohydroquinone, about 20%-95% w/w fatty acids, about 0.001/6-3% w/w α-hederin or hederagenin. In another aspect the *Terminalia arjuna* extract is standardized to contain 3% w/w arjunoglucosides. In a related aspect, the prostaglandins are selected from the group comprising prostaglandin E2 (PGE2), prostacyclin (PGI2), prostaglandin D2 (PGD2), and prostaglandin F2α (PGF2α). In another related aspect, the mammalian cells are human cells.

In another preferred embodiment, the invention discloses a composition comprising 30-60% w/w *Allium sativum* extract, 10-30% w/w *Beta vulgaris* extract, 5-15% w/w *Nigella sativa* extract and 10-30% w/w *Terminalia arjuna* extract for use as a prostaglandin transporter inhibitor. In a related aspect, the *Allium sativum* extract is standardized to contain not less than 0.3% S-allylcysteine. In another related aspect, the *Beta vulgaris* extract is standardized to contain not less than 2% nitrates. In yet another related aspect, the *Nigella sativa* extract is standardized to contain 0.1%-5% w/w thymoquinone, about 0.01%-10% w/w thymohydroquinone, about 20%-95% w/w fatty acids, about 0.001%-3% w/w α-hederin or hederagenin. In another aspect the *Terminalia arjuna* extract is standardized to contain 3% w/w arjunoglucosides. In a related aspect, the prostaglandins are selected from the group comprising prostaglandin E2 (PGE2), prostacyclin (PGI2), prostaglandin D2 (PGD2), and prostaglandin F2α (PGF2α).

In yet another preferred embodiment the invention discloses a method for the therapeutic management of hypertension in mammals, comprising step of administering an effective dose of a composition comprising 30-60% w/w *Allium sativum* extract, 10-30% w/w *Beta vulgaris* extract, 5-15% w/w *Nigella sativa* extract and 10-30% w/w *Terminalia arjuna* extract to mammals to bring about a reduction in symptoms of hypertension. In a related aspect, the management of hypertension is brought about by inhibiting/blocking prostaglandin transporter. In another related aspect, the symptoms of hypertension are selected from the group comprising elevated systolic and diastolic pressure, elevated mean arterial pressure, elevated heart rate and decreased nitric oxide levels. In another related aspect, the effective dose of the composition is 50-400 mg/kg bodyweight. In another aspect, the mammal is human. In another related aspect, the composition is formulated with pharmaceutically/nutraceutically acceptable bioavailability enhancers, antioxidants, excipients, adjuvants, diluents or carriers and administered in the form of tablets, capsules, syrups, gummies, powders, suspensions, emulsions, chewables, candies or eatables.

In yet another preferred embodiment the invention discloses a composition comprising 30-60% w/w *Allium sativum* extract, 10-30% w/w *Beta vulgaris* extract, 5-15% w/w *Nigella sativa* extract and 10-30% w/w *Terminalia arjuna* extract method for the therapeutic management of hypertension and related symptoms in mammals. In a related aspect, the management of hypertension is brought about by inhibiting/blocking prostaglandin transporter. In another related aspect, the symptoms of hypertension are selected from the group comprising elevated systolic and diastolic pressure, elevated mean arterial pressure, elevated heart rate and decreased nitric oxide levels. In another related aspect, the effective dose of the composition is 50-400 mg/kg bodyweight. In another aspect, the mammal is human. In another related aspect, the composition is formulated with pharmaceutically/nutraceutically acceptable bioavailability enhancers, antioxidants, excipients, adjuvants, diluents or carriers and administered in the form of tablets, capsules, syrups, gummies, powders, suspensions, emulsions, chewables, candies or eatables.

In another preferred embodiment the invention discloses a method for the therapeutic management of cardiovascular complications in mammals, comprising step of administering an effective dose of a composition comprising 30-60% w/w *Allium sativum* extract, 10-30% w/w *Beta vulgaris* extract, 5-15% w/w *Nigella sativa* extract and 10-30% w/w *Terminalia arjuna* extract to mammals to bring about a reduction in symptoms of cardiovascular complications. In a related aspect, the management of cardiovascular complications is brought about by inhibiting/blocking prostaglandin transporter. In another related aspect, the symptoms of cardiovascular complications are selected from the group comprising elevated systolic and diastolic pressure, elevated mean arterial pressure, elevated heart rate, and increased levels of cardiac markers. In another related aspect, the cardiac markers are selected from the group comprising Aspartate aminotransferase, Lactate dehydrogenase and Creatine kinase. In another related aspect, the effective dose of the composition is 50-400 mg/kg bodyweight. In another aspect, the mammal is human. In another related aspect, the composition is formulated with pharmaceutically/nutraceutically acceptable bioavailability enhancers, antioxidants, excipients, adjuvants, diluents or carriers and administered in the form of tablets, capsules, syrups, gummies, powders, suspensions, emulsions, chewables, candies or eatables.

In another preferred embodiment the invention discloses a composition comprising 30-60% w/w *Allium sativum* extract, 10-30% w/w *Beta vulgaris* extract, 5-15% w/w *Nigella sativa* extract and 10-30% w/w *Terminalia arjuna* for the therapeutic management of cardiovascular complications and related symptoms in mammals. In a related aspect, the management of cardiovascular complications is brought about by inhibiting/blocking prostaglandin transporter. In another related aspect, the symptoms of cardiovascular complications are selected from the group comprising elevated systolic and diastolic pressure, elevated mean arterial pressure, elevated heart rate and increased levels of cardiac markers. In another related aspect, the cardiac markers are selected from the group comprising Aspartate aminotransferase, Lactate dehydrogenase and Creatine kinase. In another related aspect, the effective dose of the composition is 50-400 mg/kg bodyweight. In another aspect, the mammal is human. In another related aspect, the composition is formulated with pharmaceutically/nutraceutically acceptable bioavailability enhancers, antioxidants, excipients, adjuvants, diluents or carriers and administered in the form of tablets, capsules, syrups, gummies, powders, suspensions, emulsions, chewables, candies or eatables.

Specific illustrative examples enunciating the most preferred embodiments are included herein below.

EXAMPLES

Example 1: Details of the Composition

The invention discloses a composition comprising 30-60% w/w *Allium sativum* extract, 10-30% w/w *Beta vulgaris* extract, 5-15% w/w *Nigella sativa* extract and 10-30% w/w *Terminalia arjuna* extract for the inhibition of PGT. The abovementioned extracts are reported to elicit cardioprotective and anti-hypertensive effects individually. Some of the medicinal properties of the above extracts are mentioned herein below:

*Allium sativum* is a well known plant used in the traditional system of Ayurveda. It is reported to elicit many therapeutic effects against different disorders which include cardiovascular diseases, regulating blood pressure, lowering blood sugar and cholesterol levels. It is also effective against bacterial, viral, fungal and parasitic infections and is reported to enhance the immune system. The plant also has anti-tumor properties (Ayaz and Alpsoy, Garlic (*Allium sativum*) and traditional medicine, Turkiye Parazitol Derg. 2007; 31(2):145-9). It houses many active molecules like allicin, saponins, phenolics and amino acids which are responsible for its biological activity. Allicin scavenges free radicals and inhibits NADPH oxidase. Allicin increases the production of $H_2S$ that results in hyperpolarisation of vascular smooth muscle cells causing vasodialation. Saponins, phenolics and s-allylcysteine directly quench the reactive oxygen species and elicit an anti-oxidant effect. The plant also produces arginine which is the precursor for the production of nitric oxide. The plant extract used in the instant invention is standardized using an in-house process to contain not less than 0.3% of s-allylcysteine.

*Beta vulgaris* (Beet root) is a common vegetable used extensively along with normal diet. It also possesses excellent therapeutic properties which include hepatoprotection, anti-diabetic, hypocholesterolemic and hypolipidemic effects, anti-bacterial and anti-oxidant properties. The plant increases the enzyme called xanthine oxidoreductase (XOR) in the red blood cells which converts nitrate to nitrite, which is then turned into nitric oxide. Nitric oxide relaxes vessel walls and has an effect on blood pressure. The extract used in the present invention was standardized using an in-house process to contain not less than 2% nitrates.

*Nigella sativa* is well known for its many therapeutic properties in the Ayruvedic, Siddha and Unani systems of medicine. The plant is reported to contain many active molecules like thymoquinone, thymohydroquinone, dithymoquinone, p-cymene, carvacrol, 4-terpineol, t-anethol, sesquiterpene longifolene, α-pinene, thymol, α hederin and hederagenin (Ahmad et al., A review on therapeutic potential of *Nigella sativa*: A miracle herb, Asian Pac J Trop Biomed. 2013; 3(5): 337-352), which are responsible for the beneficial effects of the plant. The plant is a well known antioxidant, cardiac-depressant and Calcium channel blocker which in turn affects the blood pressure and heart function. The extract used in the instant invention was standardized to contain 0.1%-5% w/w thymoquinone, about 0.01%-10% w/w thymohydroquinone, about 20%-95% w/w fatty acids, about 0.001%-3% w/w α-hederin or hederagenin.

*Terminalia arjuna* or *arjuna* is a well known medicinal plant used in the ancient Ayurvedic medicine. The bark of *Terminalia arjuna* is reported to contain many bioactive compounds, which can be tapped for use in the treatment of many diseases. Arjunoglucoside, a compound obtained from bark of *Terminalia arjuna* is well documented in literature for its cardio-protective activity. Other than its cardioprotective property, *Terminalia arjuna* and its bark extract reported for wide range of activities such as anticancer, hepatoprotective, antiviral, antioxidant, anti-asthmatic, anti-fertility, anti-diabetic, wound healing, anti-platelet and anti-coagulant, anti-bacterial and anti-fungal activity. (Saxena et al., Cytotoxic agents from *Terminalia arjuna*, Planta Med. 2007; 73(14):1486-90). It also prevents narrowing of blood vessels by reducing atherosclerotic lesions and plaque deposits in blood vessels. The extract was standardized to contain 3% w/w arjunoglucosides.

Table 1 discloses the details of the formulation and it dose.

TABLE 1

Formulation details

| Extract | Dose (mg/kg body weight) | Percentage in the composition (w/w) |
|---|---|---|
| *Allium sativum* | 250 | 50% |
| *Beta vulgaris* | 100 | 20% |
| *Nigella saliva* | 50 | 10% |
| *Terminalia arjuna* | 100 | 10% |

Example 2: Inhibition of Prostaglandin Transporter

The formulation was evaluated for its effect inhibiting the prostaglandin transporter (PGT). Kidney cell line, MDCK were seeded onto six-well plates at 30% confluence. Three days later, they were treated with 10 μM bradykinin (to increase endogenous PGE2synthesis, available in Sigma-Aldrich) in the presence of vehicle (DMSO) at 37° C. for various durations. The formulation was added at graded concentration simultaneously to the cell culture and it was further incubated for 24 hours. Media were collected for measurements of extracellular concentrations of PGE2. Cells were washed with phosphate-buffered saline twice, lysed with 250 μl of phosphate-buffered saline containing 0.1 M HCl and 0.1% Triton X-100 at room temperature for 15 min, and scraped off the plates. Cell suspensions were pipetted up and down for several times to ensure thorough lysing. Cell lysates were collected and centrifuged at 10,000 g 4° C. for 10 min. Supernatants were collected. The intracellular PGE2 in the supernatants was measured. (Yuling et al., Development of a High-Affinity Inhibitor of the Prostaglandin Transporter. The journal of pharmacology and experimental therapeutics, 2011; 339(2); 633-641). Both intracellular and extracellular PGE2 were measured using commercially available PGE2 ELISA Kit from R&D Systems according to user manual. Experiments were conducted in triplicate. Values are expressed as mean±S.E.M.

Figure 1:
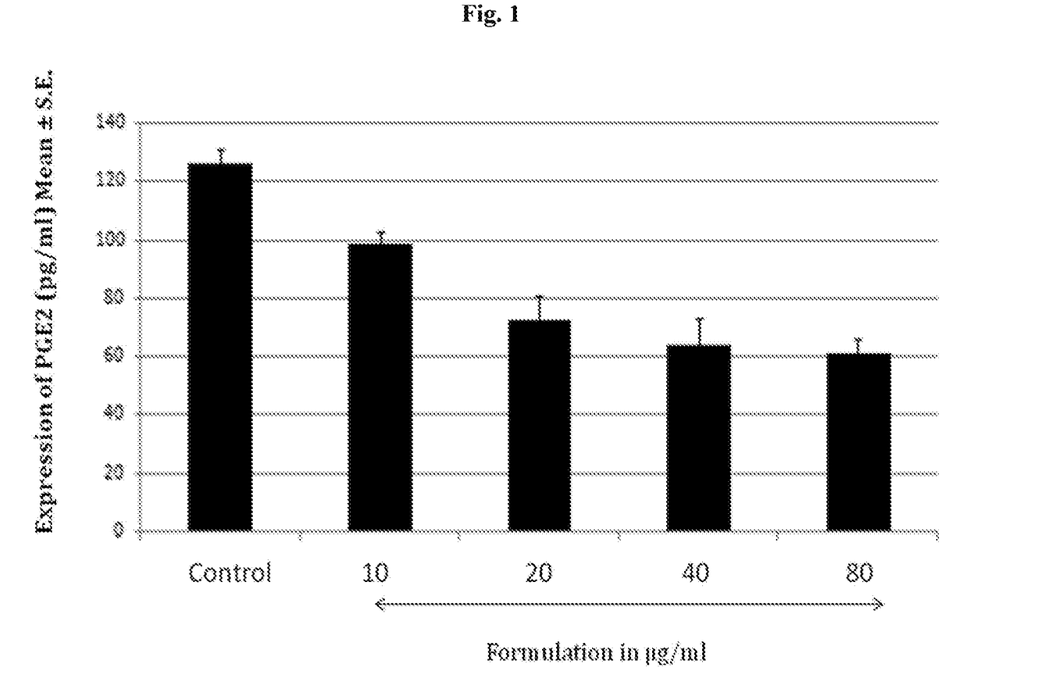
FIG. 1 is a graphical representation showing the effect of formulation on PGE2 metabolism in MDCK cells, the expression of extracellular PGE2 was analysed in the culture media
Figure 2:
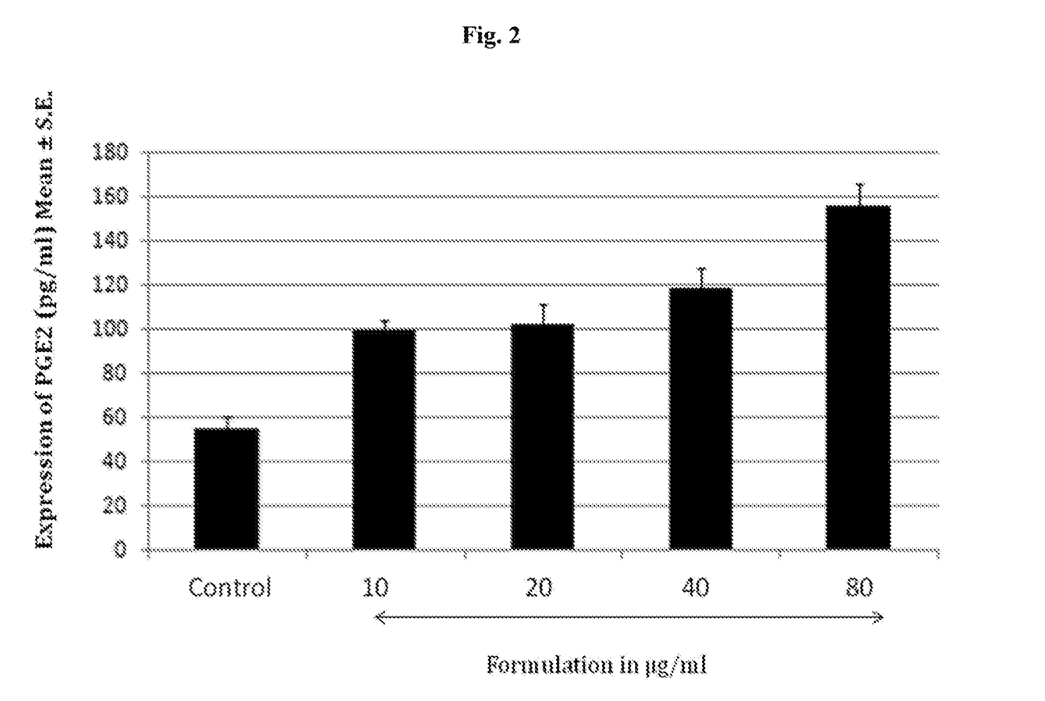
FIG. 2 is a graphical representation showing the effect of formulation on PGE2 metabolism in MDCK cells, the expression of intra cellular PGE2 was analysed in the cell lysate

In cultured MDCK cells, the formulation blocks PGE2 uptake. PGE2 triggers a vast variety of signals including inflammation, vasodilation, and angiogenesis (Weeks J R (1972) Prostaglandins. Annu Rev Pharmacol 12:317-336; Clyman R I, Mauray F, Roman C, and Rudolph A M (1978) PGE2 is a more potent vasodilator of the lamb ductus arteriosus than is either PGI2 or 6 keto PGF1alpha. Prostaglandins 16:259-264; Tsujii M, Kawano S, Tsuji S, Sawaoka H, Hori M, and DuBois R N (1998) Cyclooxygenase regulates angiogenesis induced by colon cancer cells. Cell 93:705-716). The extent of PG signaling depends, to a large degree, on its concentration at cell-surface receptors, which is determined, in turn, by the relative rates of synthesis and metabolism and the transport of PG by Prostaglandin transporter. Cell media were collected for extracellular PGE2 measurements (FIG. 1), and cells were lysed for intracellular PGE2 measurements. Decreased level of extracellular PGE2 in the formulation treated cells (FIG. 2) shows that the Prostaglandin transporter was blocked and did not allow the PGE2 formed inside the cells to come out from cells to the media.

Thus the formulation acts as an effective inhibitor of PGT and prevents the transport of prostaglandins across the membrane.

The therapeutic effect of blocking/inhibiting PGT is manifold. It plays an important role in curtailing inflammation, play a role in ovulation, mucus secretion in GI tract, vasodilatation and angiogenesis. Inhibiting PGT plays a role in hypertension by increasing PGs in circulation thereby exhibiting a vasodilatory effect (Yuling et al., Development of a High-Affinity Inhibitor of the Prostaglandin Transporter. The journal of pharmacology and experimental therapeutics, 2011; 339(2); 633-641).

The therapeutic effect of the formulation by inhibiting PGT was illustratively evaluated by its anti-hypertensive and cardioprotective effects.

Example 3: Anti-Hypertensive Effects of the Formulation

Methods

Normotensive wistar rats were used for the experiments. The rats were spontaneously induced hypertension by the administration of DOCA (deoxycorticosterone acetate) a synthetic mineralocorticoid derivative, 25 mg/kg s.c. twice a week and 1% w/v NaCl in drinking water for a period of 30 days (Model: DOCA salt induced hypertension in rats). The rats were divided into the following groups containing 6 each:

TABLE 2

Grouping

| Group | Description |
|---|---|
| I | Normal Control |
| II | Salt loaded |
| III | Formulation at 50 mg/kg bodyweight |
| IV | Formulation at 100 mg/kg bodyweight |
| V | Formulation at 200 mg/kg bodyweight |
| VI | Formulation at 400 mg/kg bodyweight |

The following parameters were estimated to evaluate the anti-hypertensive effects of the formulation Expression of PGT
Nitric oxide estimation
Blood Pressure
Heart Rate
Mean Arterial Pressure
Urine Volume
Expression of PGT Solute carrier organic anion transporter family, member 2A1 is also known as the prostaglandin transporter (PGT). Prostaglandin transporter is a member of the 12-membrane-spanning organic anion-transporting polypeptide super family of transporters. The encoded protein is involved in mediating the uptake and clearance of prostaglandins in numerous tissues. The effect of the formulation was estimated in the plasma of the rats by ELISA.

Figure 3:
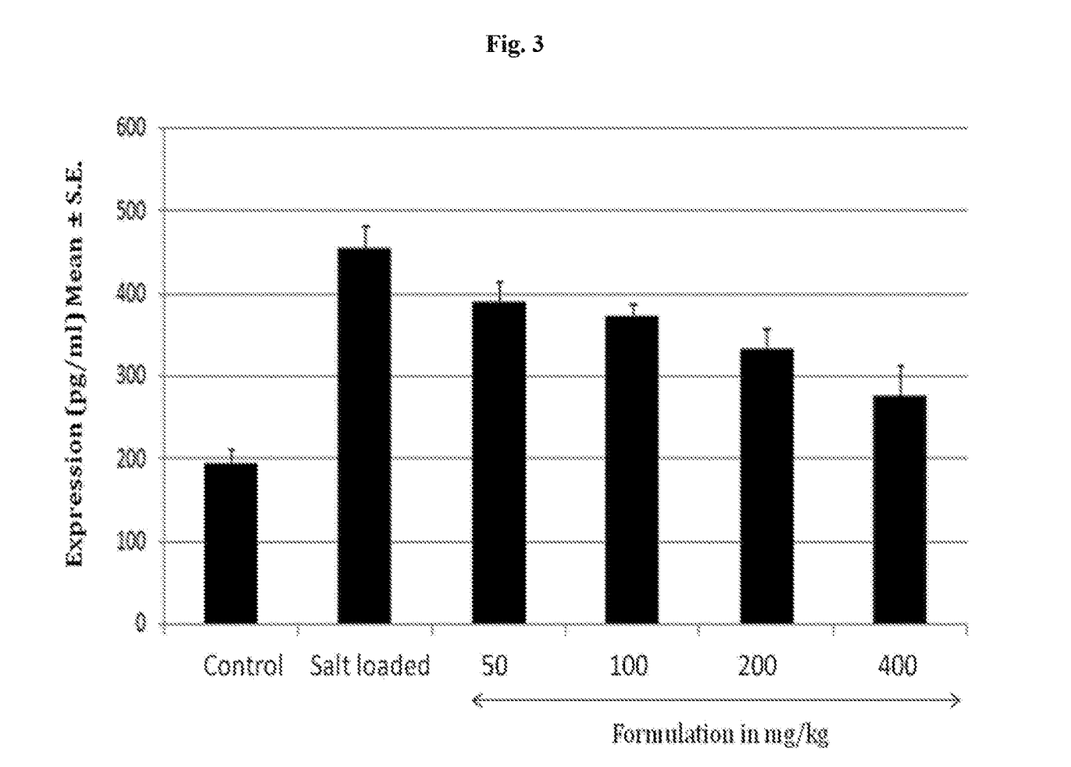
FIG. 3 is a graphical representation showing the expression of plasma PGT in rats treated with different concentrations of the formulation

The results indicated that increased salt uptake increased the expression of the PGT in plasma which was inhibited by the formulation in a dose dependant manner (FIG. 3).

Levels of Nitric Oxide

Figure 4:
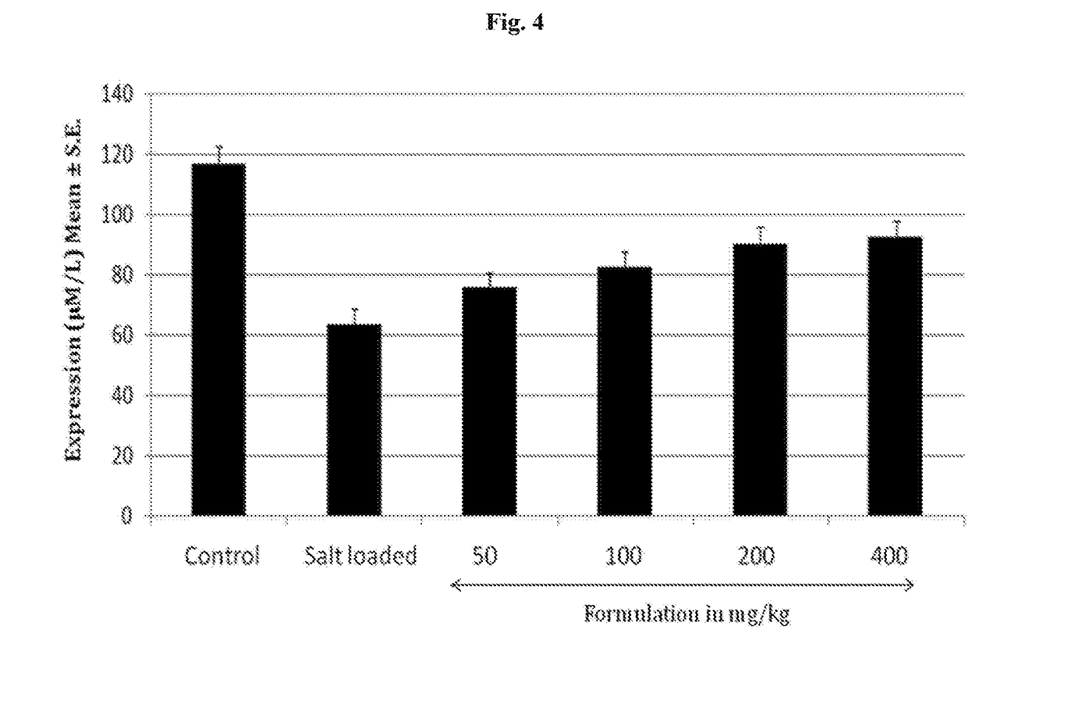
FIG. 4 is a graphical representation showing the expression of nitric oxide levels in rats treated with different concentrations of the formulation

The nitric oxide levels were significantly lower in the salt induced groups. The formulation showed increase in the expression of Total Nitric oxide in plasma in a dose dependant manner (FIG. 4)

Urine Output

Diuretics work on the kidneys by increasing the amount of salt and water that comes out through your urine. Too much salt can cause extra fluid to build up in blood vessels, raising the blood pressure. Diuretics lower blood pressure by flushing salt out of the body, taking this unwanted extra fluid with it. The diuretic effect of the formulation was tested by measuring the urine output. The results are tabulated in Table 3

TABLE 3

Urine output

| Group | Urine Volume (ml) |
|---|---|
| Normal control (Vehicle) | 5.3 ± 0.45 |
| Saline control, 5 ml | 5.4 ± 0.66 |
| Formulation (50 mg/kg, p.o.) + Saline, 5 ml | 5.4 ± 0.77 |
| Formulation (100 mg/kg, p.o.) + Saline, 5 ml | 5.8 ± 0.45 |
| Formulation (200 mg/kg, p.o.) + Saline, 5 ml | 6.4 ± 0.49 |
| Formulation (400 mg/kg, p.o.) + Saline, 5 ml | 6.05 ± 0.34 |

The formulation at 200 mg/kg effectively increased the urine output indicating that it acts as an efficient diuretic.

Blood Pressure, Heart Rate and Mean Arterial Pressure

Figure 5A:
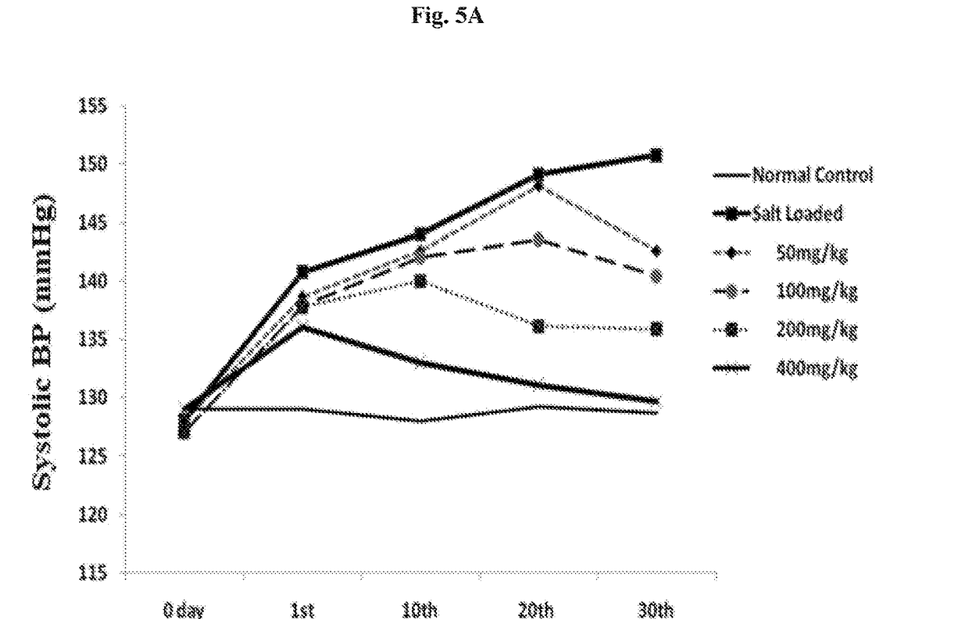
FIG. 5A is a graphical representation showing the systolic BP in rats treated with different concentrations of the formulation
Figure 5B:
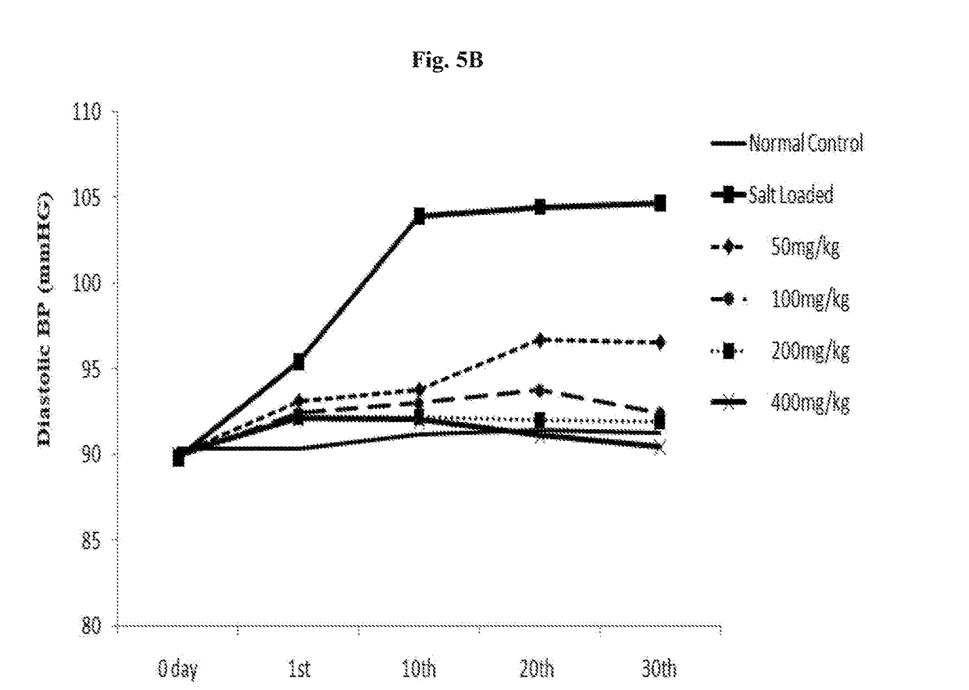
FIG. 5B is a graphical representation showing the diastolic BP in rats treated with different concentrations of the formulation
Figure 6:
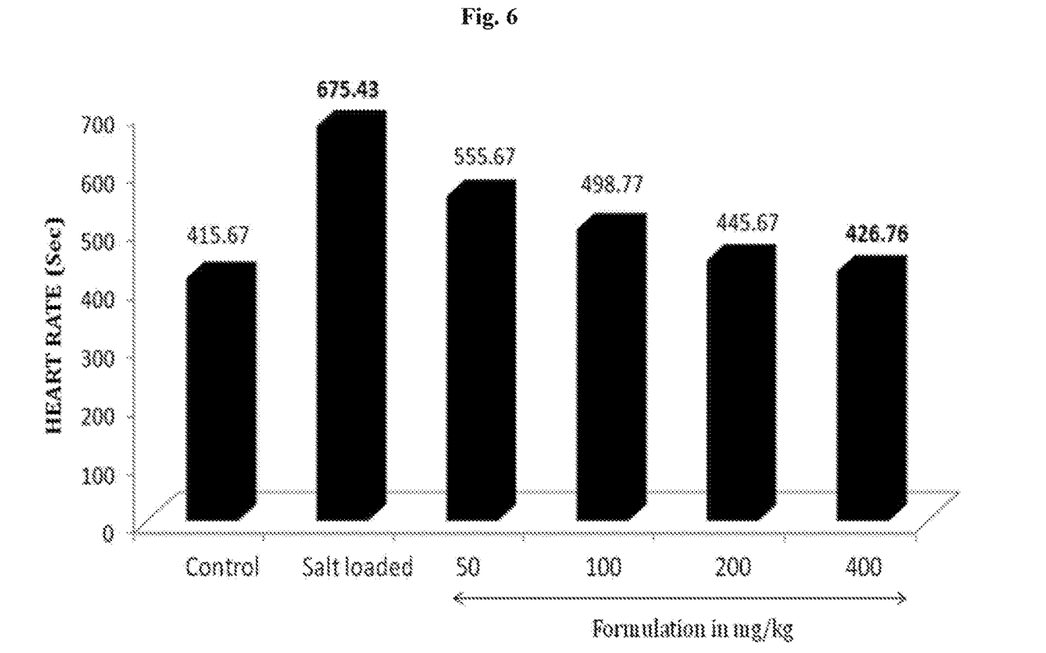
FIG. 6 is a graphical representation showing the heart rate in rats treated with different concentrations of the formulation
Figure 7:
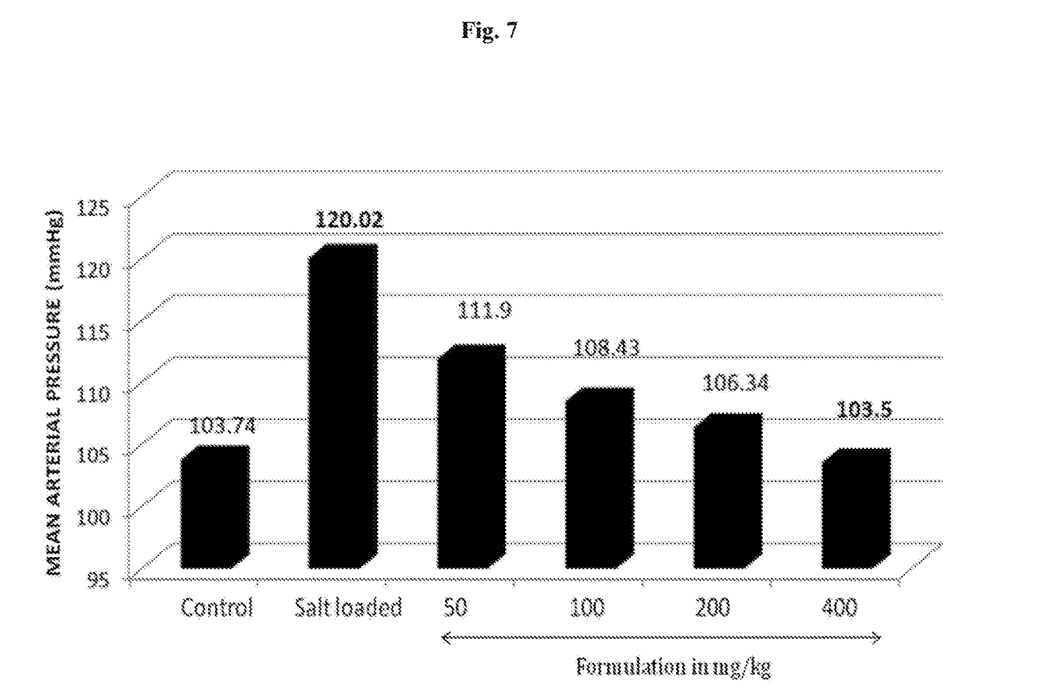
FIG. 7 is a graphical representation showing the mean arterial pressure in rats treated with different concentrations of the formulation

The Blood Pressure, Heart Rate and Mean Arterial Pressure were estimated using standard protocol. Increase in salt, increased the levels of systolic and diastolic blood pressure, heart rate and Mean arterial pressure. The formulation, by inhibiting PGT effectively lowered the Blood Pressure (FIGS. 5A and 5B), Heart Rate (FIG. 6) and Mean Arterial Pressure (FIG. 7) in a dose dependant manner indicating that it is a very effective anti-hypertensive composition.

Example 4: Cardioprotective Effects of the Formulation

The formulation comprising the plant extracts was very effective in inhibiting PGT thereby eliciting an anti-hypertensive effect. The formulation was effective in reducing the heart rate, systolic and diastolic blood pressure. Since elevated heart rate is related to the development of cardiovascular complications, the lowering of heart rate by the formulation through inhibition of PGT can confer a cardioprotective effect. Thus, the cardio protective effect by of the formulation was tested in Isoproterenol induced cardiotoxicity in rats.

Isoproterenol [1-(3, 4-dihydroxyphenyl)-2-isopropylamino ethanol hydrochloride](ISO), a synthetic catecholamine and β-adrenergic agonist, causes severe oxidative stress in the myocardium, resulting in infarct-like necrosis of the heart muscle. It is also known to generate free radicals and to stimulate lipid peroxidation. The following cardiac markers were evaluated:
a) Aspartate aminotransferase (AST).
b) Lactate dehydrogenase (LDH).
c) Creatine kinase-MB (CK-MB).

Figure 8:
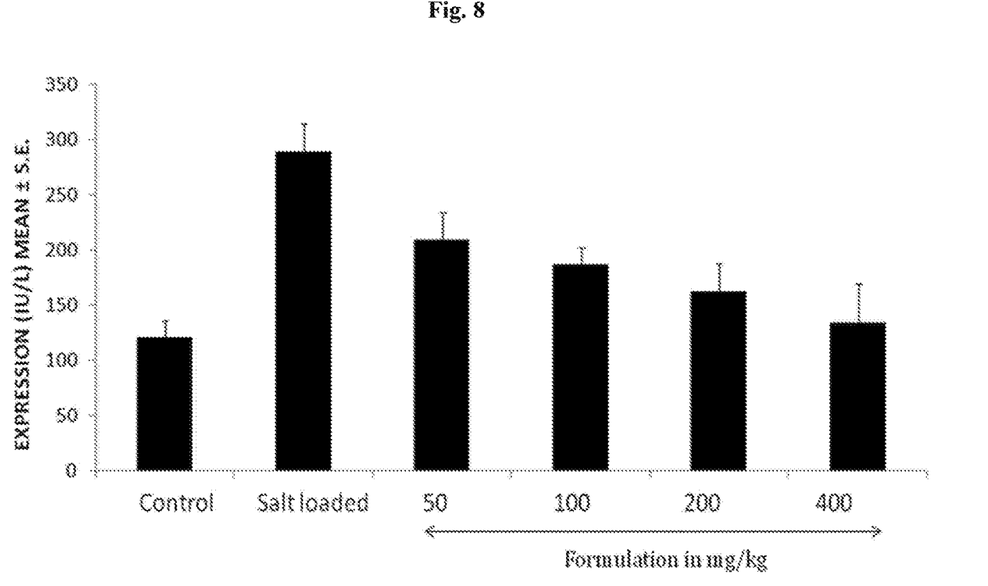
FIG. 8 is a graphical representation showing the AST levels in rats treated with different concentrations of the formulation
Figure 9:
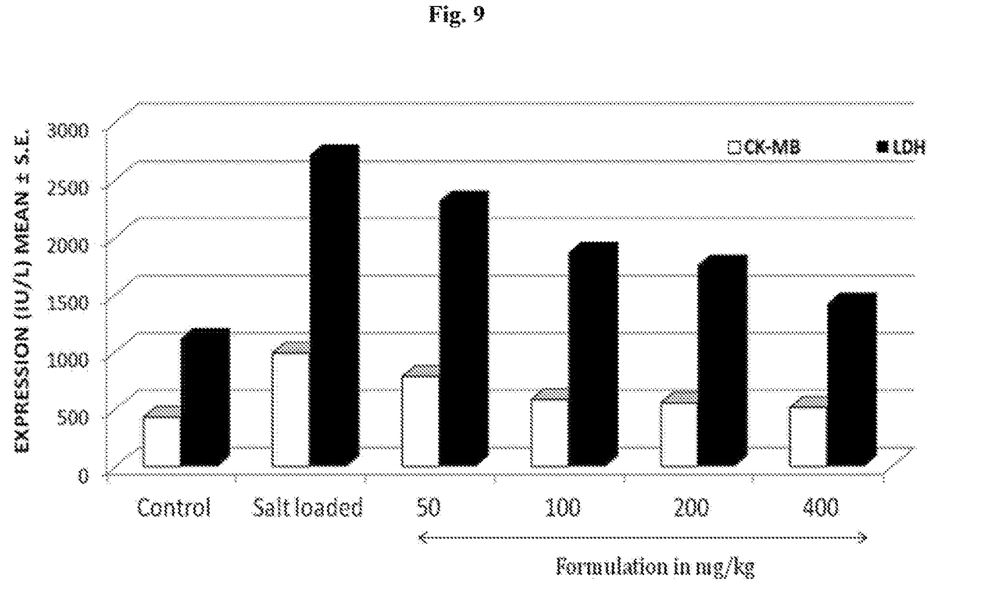
FIG. 9 is a graphical representation showing the LDH and CK-MB levels in rats treated with different concentrations of the formulation

AST occurs in all human tissues and present in large amounts in liver, renal, cardiac and skeletal muscle tissue. The level increases in myocardial infarction, muscular dystrophy and liver diseases. The increase in the AST levels in the present invention indicates damage to the heart due to increased cardiotoxicity due to Isoproterenol. The formulation effectively reduced AST levels (FIG. 8) thereby indicated that it mitigates the cardiotoxicity developed due to increased salt intake. Similarly, the LDH and CK-MB levels (FIG. 9) also returned to normal in rats administered with the formulation, indicating its cardioprotective effects.

The results indicated that the formulation is an excellent PGT inhibitor. The formulation also conferred related therapeutic benefits of PGT inhibition by being an anti-hypertensive by reversing the increase in heart rate, blood pressure and Mean arterial pressure close to the normal levels. The formulation is also confers cardioprotective effects by decreasing the elevated cardiac markers close to near normal levels.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method for inhibiting prostaglandin transporter in mammalian cells, said method comprising step of bringing into contact mammalian cells expressing prostaglandin transporter with a composition essentially consisting of 30-60% w/w *Allium sativum* extract is standardized to contain not less than 0.3% S-allylcysteine, 10-30% w/w *Beta vulgaris* extract standardized to contain not less than 2% nitrates, 5-15% w/w *Nigella sativa* extract standardized to contain 0.1%-5% w/w thymoquinone, about 0.01%-10% w/w thymohydroquinone, about 20%-95% w/w fatty acids, about 0.001%-3% w/w α-hederin or hederagenin, and 10-30% w/w *Terminalia arjuna* extract standardized to contain 3% w/w arjunoglucosides.

2. The method as in claim 1, wherein the prostaglandins are selected from the group comprising prostaglandin E2, prostacyclin, prostaglandin D2, and prostaglandin F2a.

3. The method as in claim 1, wherein the mammalian cells are human cells.

* * * * *